Figure 1:
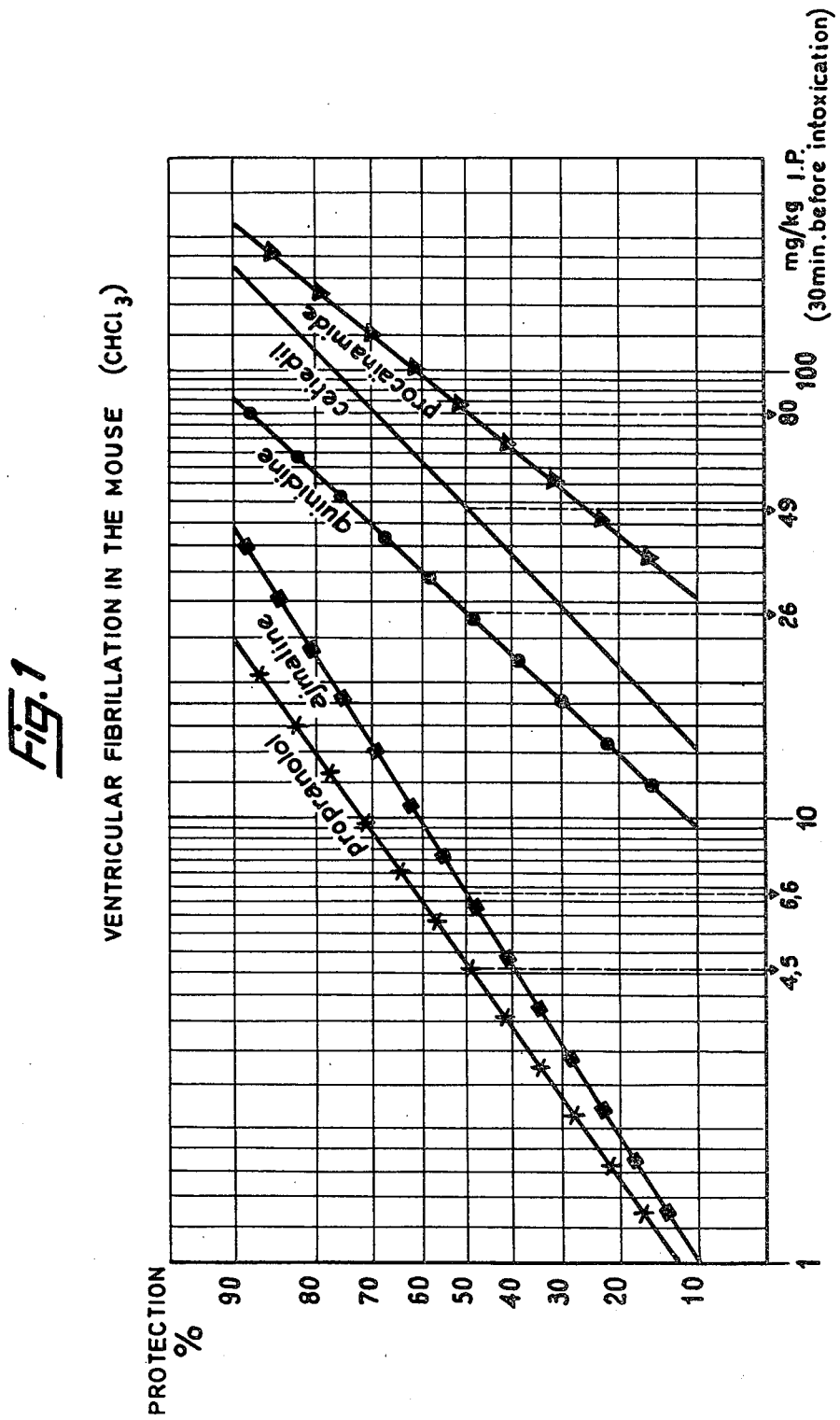

United States Patent [19]

Aurousseau

[11] 4,377,592

[45] Mar. 22, 1983

[54] ANTIARRHYTHMIC ACTIVITY OF CETIEDIL

[75] Inventor: Michel E. M. Aurousseau, Paris, France

[73] Assignee: Innothera, Arcueil, France

[21] Appl. No.: 88,198

[22] Filed: Oct. 23, 1979

[51] Int. Cl.³ .............................................. A61K 31/38
[52] U.S. Cl. .................................................... 424/275
[58] Field of Search ........................................ 424/275

[56] References Cited

FOREIGN PATENT DOCUMENTS 1384022 2/1975 United Kingdom .
1392671 4/1975 United Kingdom .

OTHER PUBLICATIONS

Haring et al., J. Clin. Pharm., Therapy & Toxicology, vol. 18, No. 11, 1980, pp. 467–481, (Citing Szekeres, Actualites Pharmacologiques, vol. 19, 1966, p. 149).
Szekeres, Actualites Pharm., vol. 19, 1966, pp. 149–185.
Simaan, The J. of Pharm. & Exptl. Therap., vol. 198, 1976, pp. 176–186.
Martindale, The Extra Pharm., The Pharm. Press, London, 26th Ed., 1972, pp. 1271–1272.

*Primary Examiner*—Anna P. Fagelson
*Attorney, Agent, or Firm*—Merriam, Marshall & Bicknell

[57] ABSTRACT

New method for treating cardiac arrhythmia by administering cetiedil to a patient.

3 Claims, 15 Drawing Figures

VENTRICULAR TACHYCARDIA INDUCED BY OUABAIN

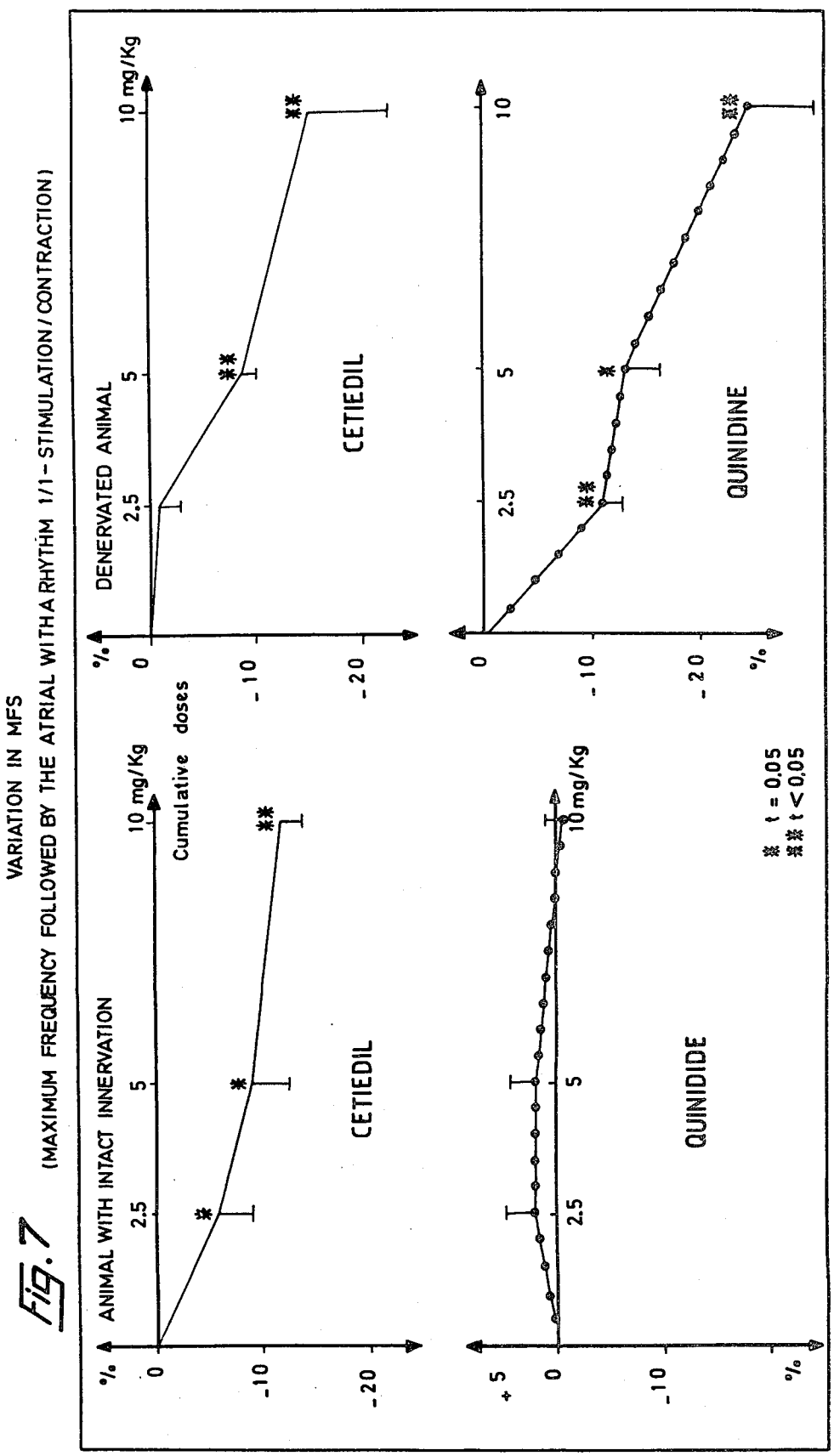
Fig. 7 VARIATION IN MFS (MAXIMUM FREQUENCY FOLLOWED BY THE ATRIAL WITH A RHYTHM 1/1 – STIMULATION / CONTRACTION)

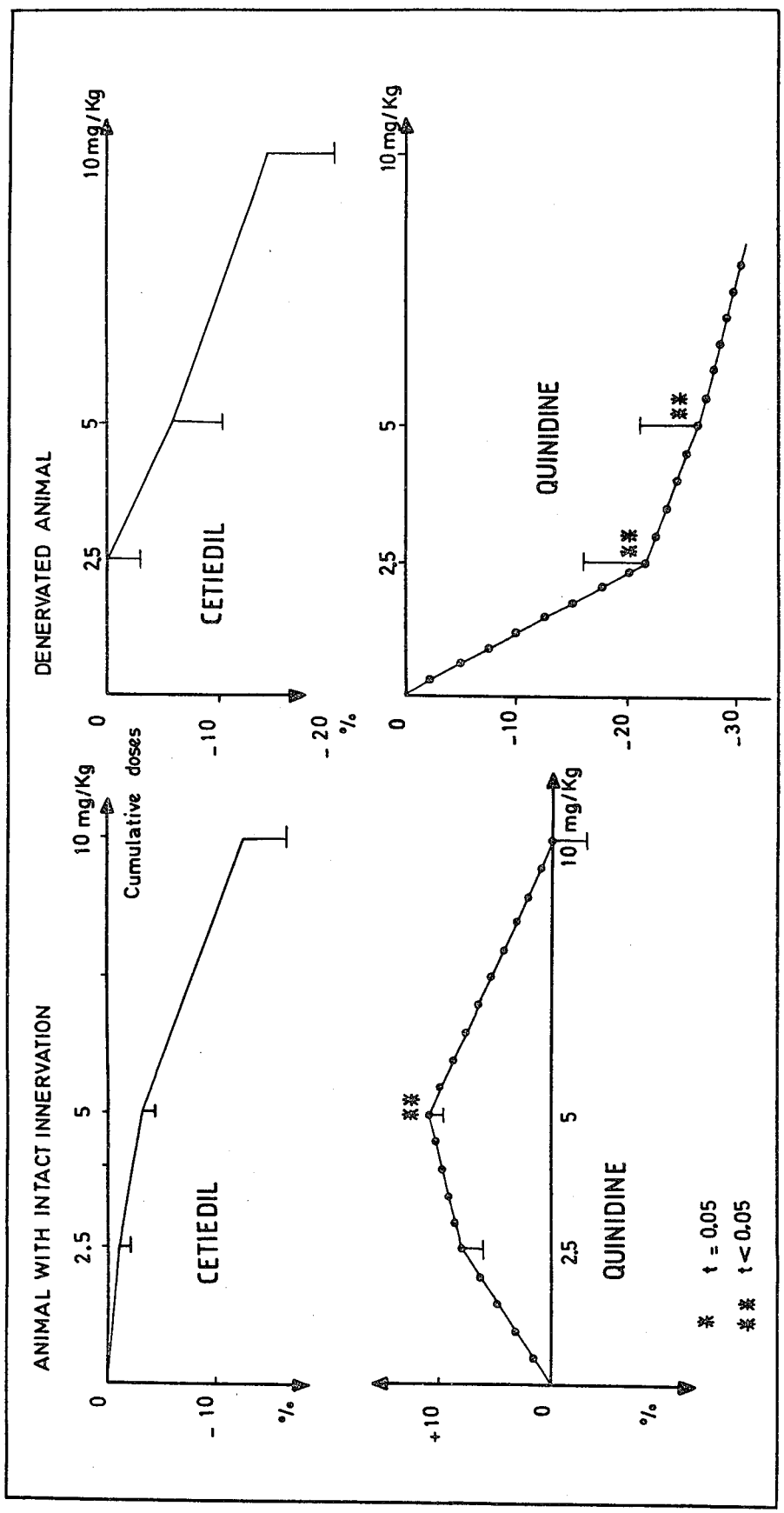

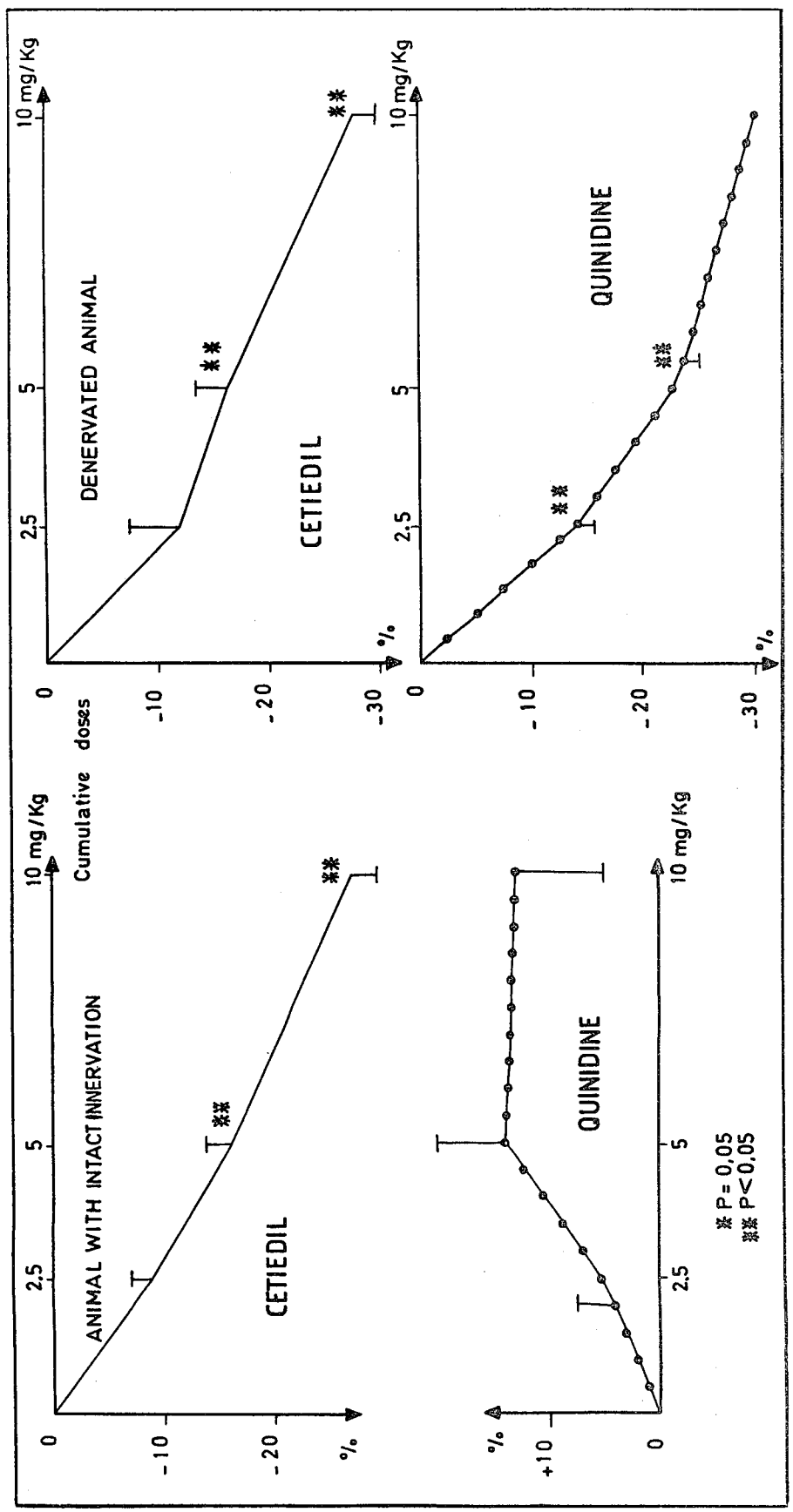

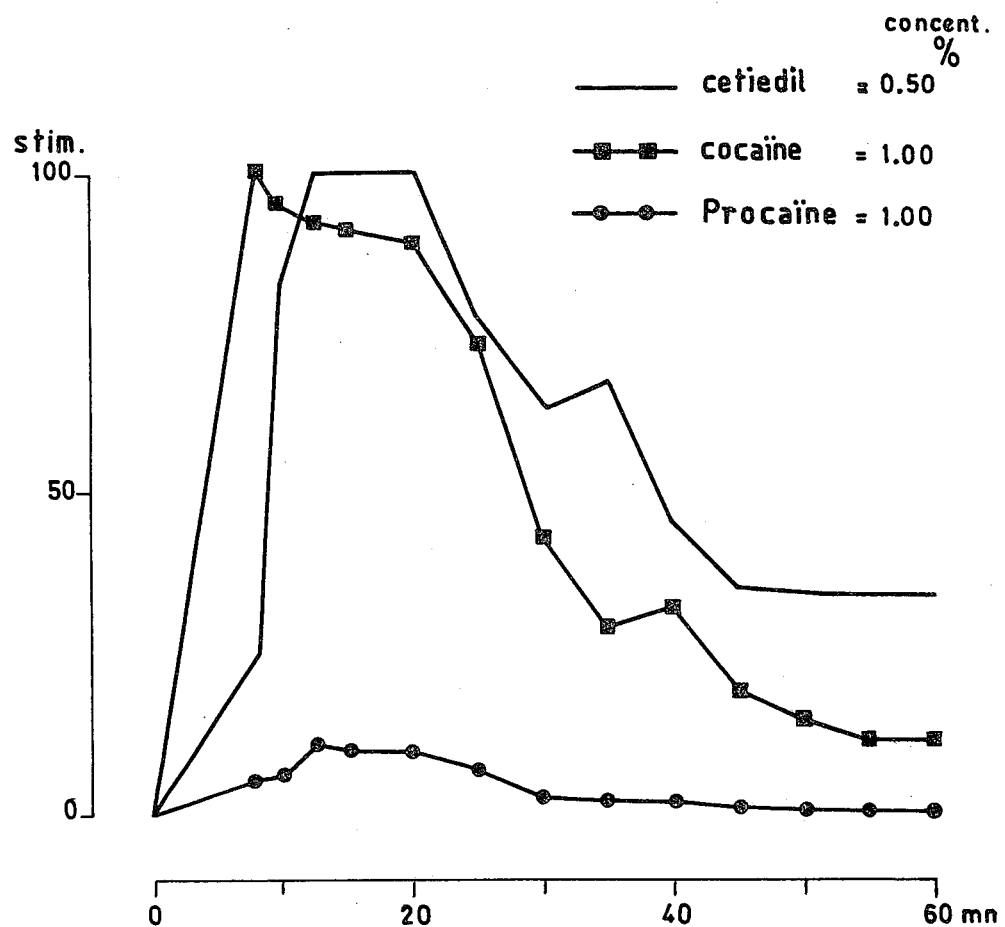

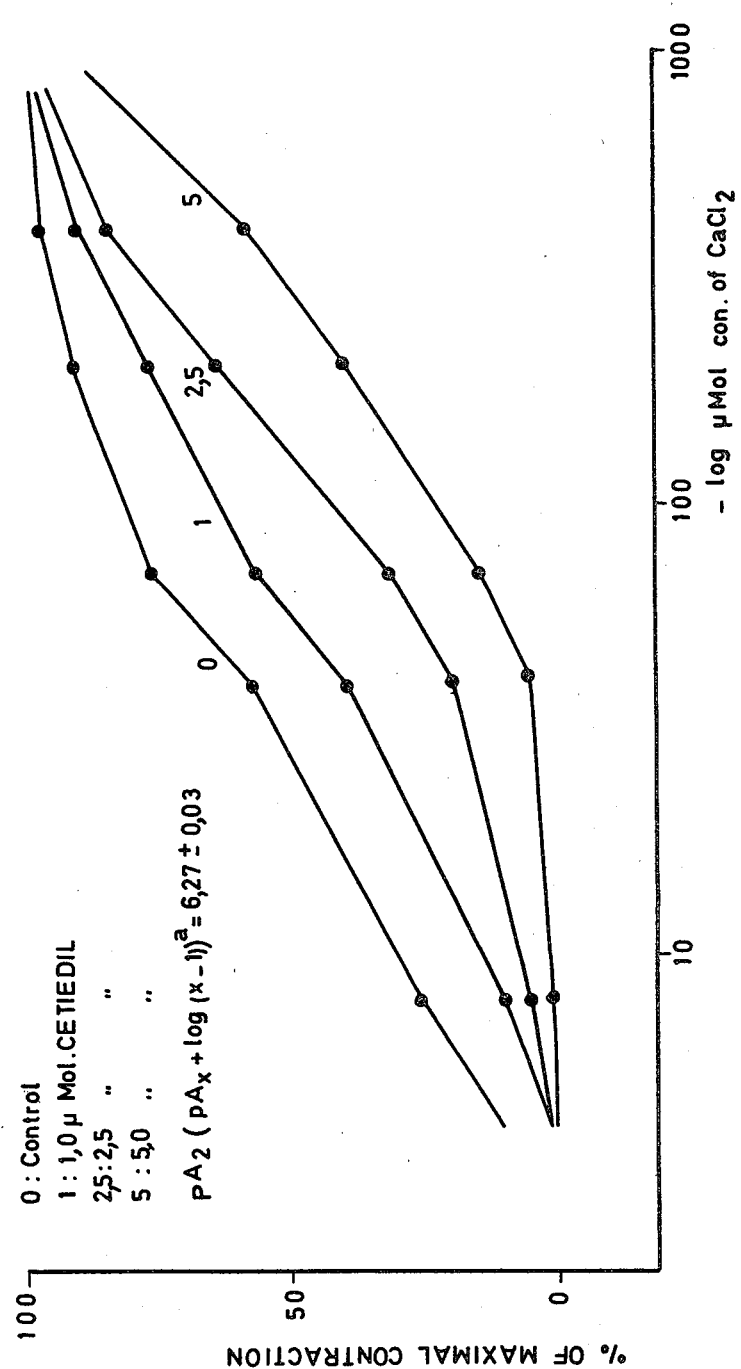

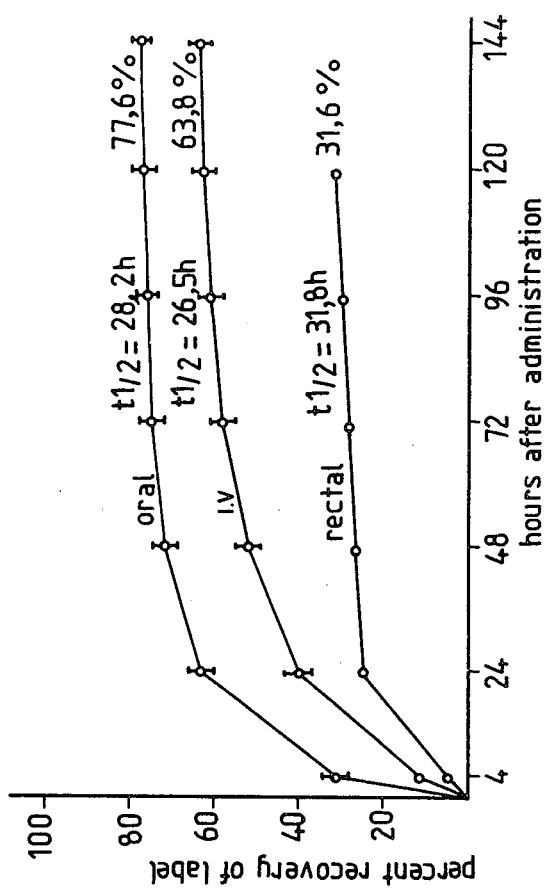
Fig. 13 CUMULATIVE EXCRETION OF LABEL IN URINE AFTER I.V. ORAL AND RECTAL ADMINISTRATION OF 0,25 mg CETIEDIL-$C^{14}$
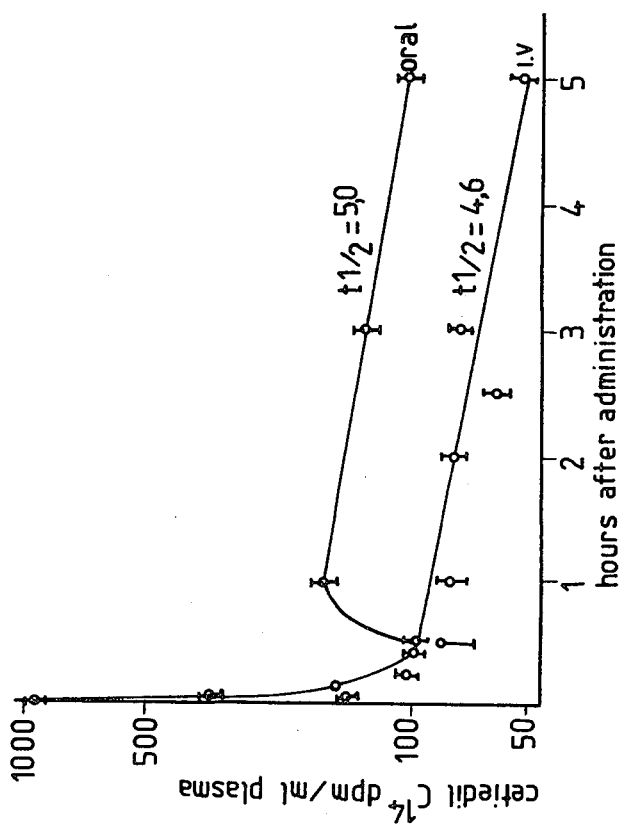
Fig. 12 PLASMA CONCENTRATION CURVES 0,25 mg CETIEDIL-$C^{14}$ AFTER I.V. AND ORAL ADMINISTRATION CUMULATIVE EXCRETION OF LABEL IN FECES AFTER I.V. ORAL AND RECTAL ADMINISTRATION OF 0,25mg CETIEDIL-$C^{14}$ Fig. 15 — HYPERTENSIVE AND ISCHEMIC CARDIOPATHY, SINUSAL RHYTHM, AURICULAR EXTRASYSTOLS, AND BLOCKED P. WAVES
BEFORE INJECTION
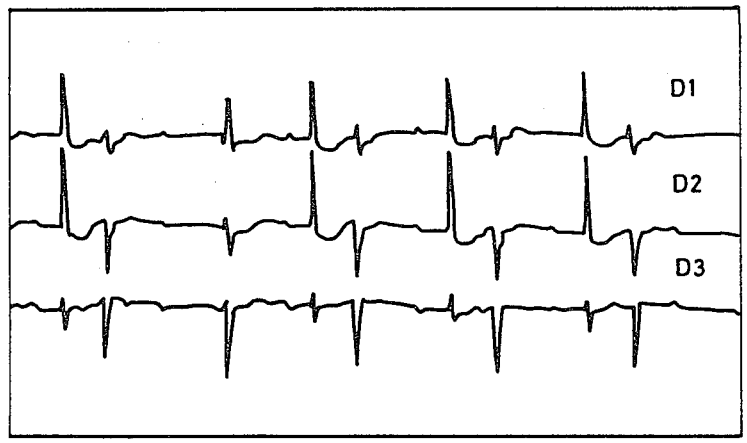
AFTER INJECTION
THREE HOURS AFTER INJECTION OF 50 mg – I.V. INFUSION OF CETIEDIL DURING HALF AN HOUR
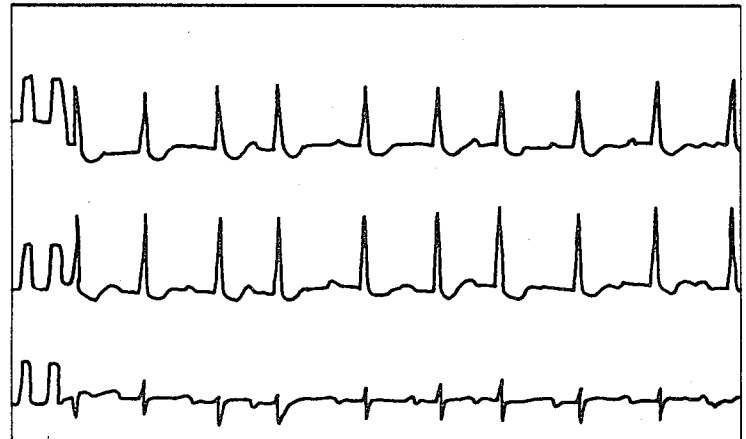

4,377,592

ANTIARRHYTHMIC ACTIVITY OF CETIEDIL

The invention relates to a method for treating disturbances of cardiac rhythm, i.e. cardiac arrhythmia, which comprises administering cetiedil to a patient.

Cetiedil is the citrate monohydrate of α-cyclohexyl-3-thiopheneacetic acid 2-(hexahydro-1H-azepin-1-yl)ethyl ester (or the citrate monohydrate of α-cyclohexyl-α(3-thienyl)acetic acid 2-hexamethyleneiminoethyl ester), which has been described i.a. in French Pat. No. 73.07505 and corresponding U.K. Pat. No. 1,392,671, and was indicated for treating spasmodic and painful conditions of the digestive, biliary and urinary tracts, of the arteriovenous system and of the pelvic organs, and particularly the pathological conditions of the peripheral arterial vascular system. It has generally been used in the treatment of peripheral vascular disturbances.

Unexpectedly, it has now been found that cetiedil is an effective antiarrhrythmic agent. It has been subjected to pharmacological investigation and then to clinical investigation which are reported hereinafter.

PHARMACOLOGICAL SECTION

A-PREVENTION "IN VIVO" OF AN EXPERIMENTAL DISRHYTHMIA BY CHEMICAL AGENTS

I-Chloroform-induced ventricular fibrillation in the mouse (a) Experimental protocol.

In this technique first described by LAWSON, J. W. in J. Pharm. Exp. Ther. 1968, 160, 22 and Vargaftig, B. B. et al in Eur. J. Pharmacol. 1969, 6, 49, the inhalation of chloroform vapour produced in the mouse apnea followed by ventricular fibrillation.

The mechanism of this technique remains unknown. Sympathetic hyper-activity, associated with hyper-tension, has been suggested as a activating factor, but this mechanism is open to discussion, (Vargaftig, Supra).

(b) Results (FIG. 1)

The $ED_{50}$ is of the order of 50 mg/kg IP, being relatively high but the extreme "severity" of the test used should be borne in mind. The latter has the advantage of being simple, rapid and reproducible but whilst it permits the selection of the principal antidysrhythmic agents (Ajmaline: $ED_{50}$: 6.6 mg/kg IP Quinidine $ED_{50}$: 26.00 mg/kg IP-Procainamide: $ED_{50}$: 80 mg/kg IP), it is also positive with other substances (Linee, P. H., These Doct. Pharmacie, Reims, 1975) such as Atropine: $ED_{50}$: 100 mg/kg IP-Yohimbine: $ED_{50}$: 10 mg/kg-IP-or Imipramine: $ED_{50}$: 30 mg:kg IP.

II-Polymorphous arrhythmias induced in the guinea-pig anaesthetised using a combination of Adrenaline and petrol ether (a) Experimental protocol Adrenaline in high dosage is a powerful arrhythmogenic stimulus to a myocardia induced by petrol ether, as recognized in the guinea-pig by LE MARECHAL J., Thesis Doct. Med., Reims, 1963.

The selectivity is open to discussion since it is positive for the majority of classical antidysrhythmic agents, but also phentolamine, imipramine and adrenergic inhibitors.

Disturbances induced by a combination of adrenaline and petrol ether may be attributed to vagal hyperactivity and hypertension provoked by adrenaline on a "sensitized" myocardia (LINEE, supra) as would also be the case with chloroform (Advenier, C., Thesis Doct. Pharm., Paris, 1971 and Han, J. et al, Circulation Res. 1964, 14, 44)

Figure 2:
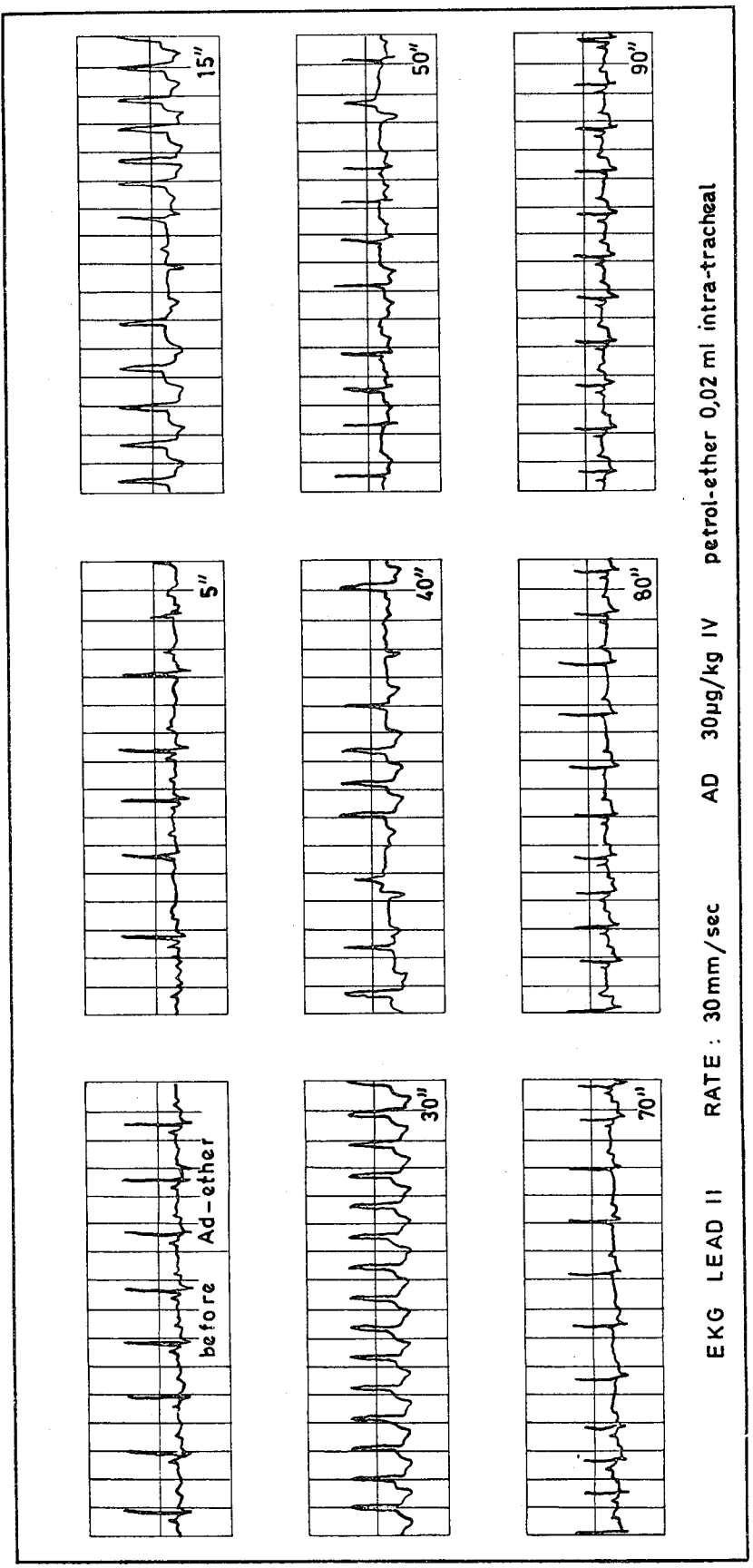
Figure 3:
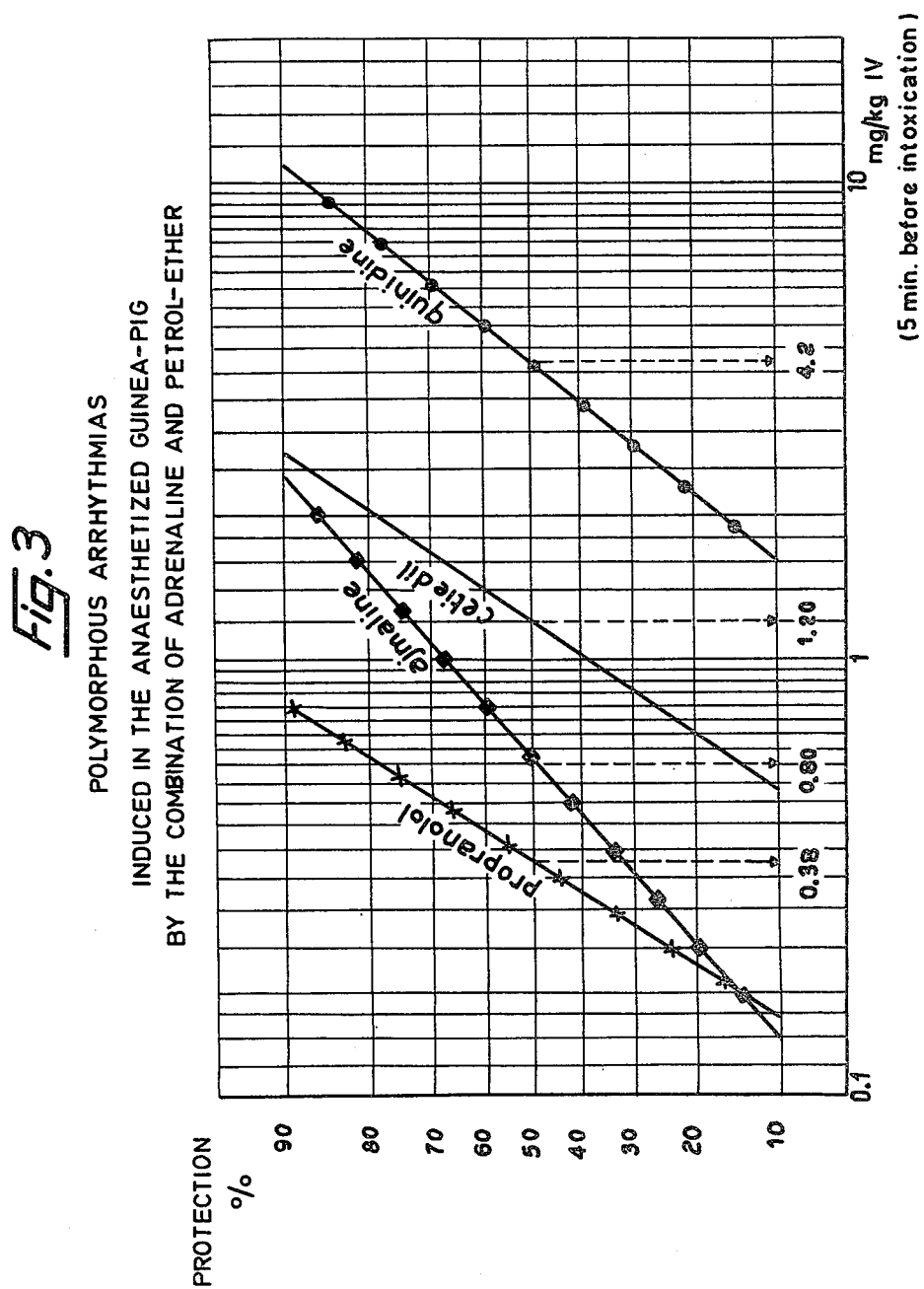

Results (FIGS. 2 and 3; table 1)

The $ED_{50}$ is of the order of 1.2 mg/kg after a 5 minutes latent period. In relation to the "I" index of $LD_{50}$ IV/$ED_{50}$, the activity of CETIEDIL lies between that of procainamide and propranolol on one hand, and that of Ajmaline on the other hand.

III-Calcium induced ventricular fibrillation in the rat (a) Experimental protocol According to MALINOW, M. R., et coll. Acta. Physiol Latino. Americ. 1953, 3, 216 and Acta. Cardiol., 1954, 9, 107, ions such as magnesium, potassium, barium and above all calcium may, under certain conditions and in high dosage, provoke the development of atrial flutter, ventricular tachycardia, ventricular fibrillation and death.

Using the anaesthetized rat, 200 mg/kg of $CaCl_2$ was injected two minutes after the substances to be tested. The ECG was recorded continuously in lead II.

Figure 4:
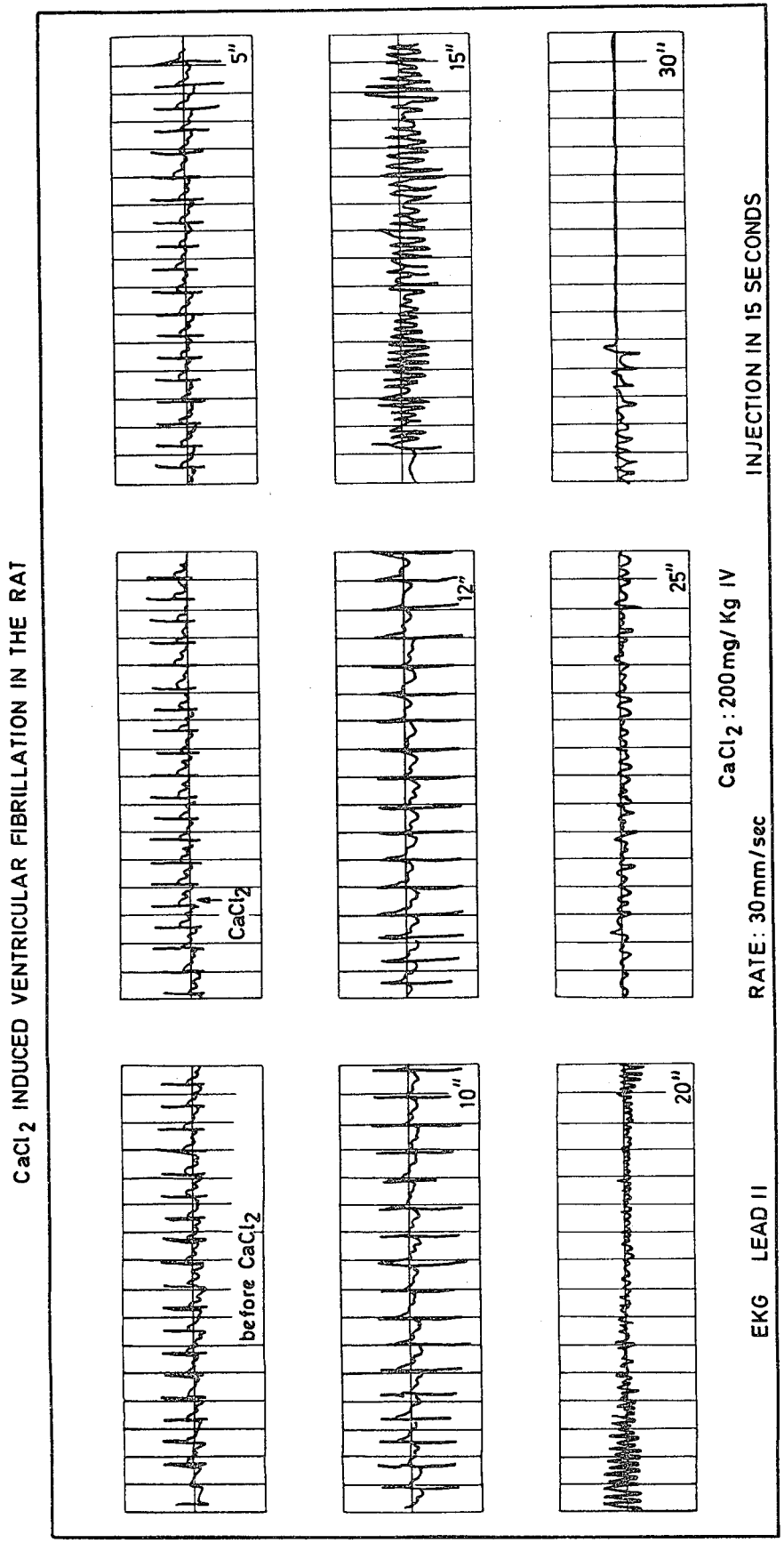

(b) Results (FIG. 4; Tables 2 and 3)

The $AD_{50}$ protecting 50% of the animals against ventricular fibrillation and death is 3.5 mg/kg. The reference substances used are less active if the relative activity is compared. It may be noted that Ajmaline at the dose of 5 mg/kg protected all of the animals against ventricular fibrillation but none against death.

IV-Ouabain induced tachycardia and arrhythmia (a) Experimental protocol

This test is used to determine the dose of ouabain administered by slow infusion necessary to obtain the appearance of ventricular extrasystoles. The animal used was the guinea pig and the substances were administered intravenously.

(b) Results (Table 4)

In these experiments, CETIEDIL was associated with a significant increase, dose "related" (5 and 10 mg/kg) in the threshold before the development of cardiac disturbances. Under the same conditions, Ajmaline is active at 2.5 mg/kg, Quinidine and Procainamide at 5 mg/kg.

(c) Experimental protocol in the dog

The method used is that of LUCCHESI and HARDMAN, J. Pharmacol. Exp. Ther. 1961, 132, 372–381. Ventricular tachycardia was obtained by the sequential administration of Ouabain until a permanent ventricular tachycardia developed. Following observation of the effect of the substance, the reappearance of this ventricular tachycardia following the injection of insulin was confirmed, thereby showing the persistence within the heart of a toxic dose of Ouabain (Average dose of Ouabain 71.25 γ kg IV).

Figure 5:
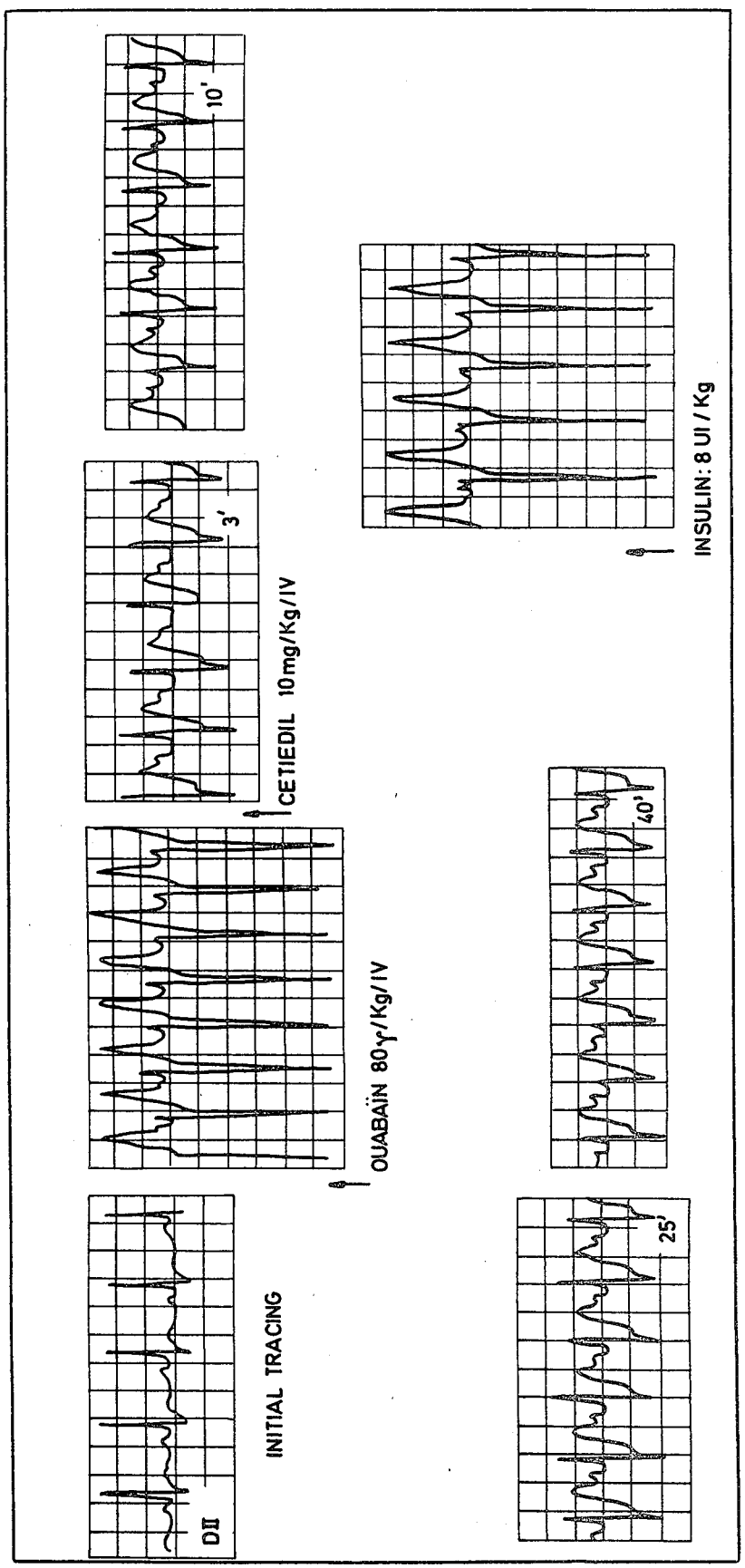

(d) Results (FIG. 5)

The average dose of CETIEDIL required to obtain a return to sinus rhythm for a period of more than 30 min is 10 mg/kg IV. For Quinidine sulfate, this dose is 6.4 mg/kg with a duration of less than 30 min.

B-DETERMINATION OF MECHANISM OF ACTION MEMBRANE STABILIZING EFFECT

A certain number of antiarrhythmic agents, such as quinidine and substances of group 1 of VAUGHAN-WILLIAMS classification, have membrane stabilizing properties with a negative bathmotropic effect. It was for this reason that such an effect was sought in CETIEDIL.

STUDY OF DROMOTOPIC EFFECT AND ATRIO-VENTRICULAR CONDUCTION (a) Experimental protocol The technique of DAWES (modified by ALLIES ET AL.) was used with the isolated guinea-pig atrial, and the technique of DUCHENE-MARULLAZ, J. Pharmacol. Paris, 1970, 1, 539, in the anaesthetized dog. This method is used to study the permeability of atrio-ventricular conduction, and thus more precisely conduction at the level of Tawara's nod.

(b) Results

Figure 6:
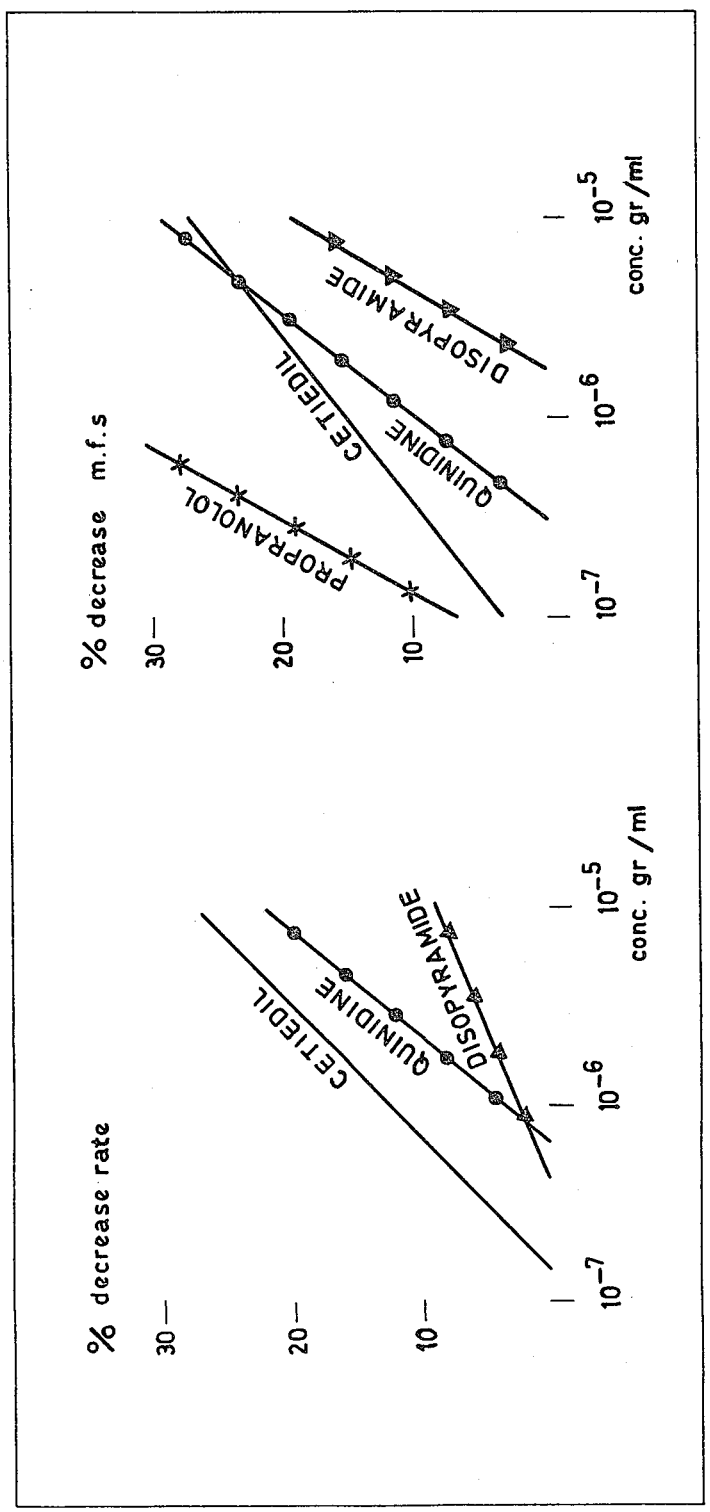

Isolated and stimulated atrial: Table 5, FIG. 6.

Atrio-ventricular conduction in the dog: FIGS. 7, 8 and 9. Using the isolated and stimulated guinea-pig atrial, CETIEDIL at a concentration of $1.10^{-6}$ had a negative bathmotropic effect identical to that of Quinidine and less than that of Propranolol.

With regard to atrio-ventricular conduction in the dog, CETIEDIL produces a significant depression which was proportional to the dose injected. This negative dromotropic effect was not altered by denervation. By contrast, the bathmotropic effect of Quinidine is not changed in the intact animal but is reversed in the animal following denervation. Depression of atrio-ventricular conduction is significant and proportional to the dose administered.

SURFACE LOCAL ANAESTHESIA IN THE RABBIT (a) Experimental protocol

For the purpose of this study, the classical technique of REGNIER J., Thesis Doct. Med., Saint-Dizier, 1929, condified by LECHAT P., Thesis Doct. Med. Paris, 1955, was used. This consists of repeating touching of the rabbit cornea until an oculo-palpebral reflex is obtained. It should be noted that CETIEDIL, in common with the reference substances, was used in the form of the HCl Salt.

(b) Results (FIG. 10; Table 6)

CETIEDIL, in local installation at a concentration of 0.5%, produced complete local anaesthesia lasting for 15 min. The same effect is obtained with 1 p.100 of cocaine or Propranolol, procaine being only half less active.

STUDY OF ANTAGONISM AGAINST CALCIUM (a) Experimental protocol

Fragments of aorta removed from rats are immersed in survival fluid in the presence of carbogene at 37° C. By modifying the ionic equilibrium of the survival medium, it was possible to study the effects of CETIEDIL on contraction of the aortic fragments induced by depolarisation with potassium or calcium.

(b) Results (Table 7; FIG. 11)

In vitro, CETIEDIL inhibited the contraction of rat aortic fragments induced by potassium depolarisation, with a pD2 of 5.23. In other words, the force of contraction recorded in the presence of 1.26 mM of calcium was reduced by half with 6 μm of CETIEDIL. In this particular test, CETIEDIL was approximately 500 times more active than procaine. The antagonism may be attributed to competitive inhibition of calcium exchange at the level of contractile sites. The dose/effect curve of contraction of the rat aortic fragment in relation to the calcium concentration is displaced toward the right in the presence of CETIEDIL, and the inhibition is overcome by an excess of calcium. The $pA_2$ (Aeriens, E. J. et al., Arch. Int. Pharmacody., 1957, CX, No. 2, 3) of this competitive inhibition is 6.27: the amount of calcium necessary to provoke half of the maximum contraction should be doubled in the presence of 0.54 μM of CETIEDIL.

PHARMACOLOGICAL DISCUSSION

The results obtained would indicate that CETIEDIL posesses antiarrhythmic properties. With regard to VAUGHAN-WILLIAMS classification, it may be said that the substance cannot to be included in group 2 (substances acting on the sympathethic nervous system) since tests involving chloroform induced fibrillation of adrenergic origin in the mouse indicated the slight activity only of the substance, ten times less powerful than propranolol.

An α-lytic mechanism not being conceivable, it would appear that the substance acts by virtue of its negative bathmotropic power, reviewed in vitro, by tests involving the stimulated atrial. It may also be noted that polymorphous arrhythmias obtained in the guinea pig by combination of adrenaline and petrol-ether are notably decreased by the substance which proves to be only three times less active than the reference β-blocker. It may here be considered that the para-sympatholytic effect of the substance, although slight, is responsible for this activity, in association with the negative bathmotropic action already mentionned.

It might as well be considered that CETIEDIL may not be classified in group 2 of VAUGHAN-WILLIAMS classification (sympatholytic and α-adrenolytic). By contrast, it may certainly be included in group 1 of the membrane stabilizing agents, along side in particular quinidine and local anaesthetics.

In fact, the substance has local anaesthetic effects which are twice as great as those of cocaine. Furthermore, it has been seen to be 500 times more active than procaine as an inhibitor of vascular contraction due to potassium depolarization. It should therefore stabilize the myocardia cell membrane, decreasing reactivity, the rate of increase and the amplitude of action potentials related to ion permeability, in particular potassium.

This results in bathmotropic effect, shown experimentally using the stimulated atrial, and negative dromotropic effects. The latter has been seen in the study of atrio-ventricular conduction in dog during which the maximum rate transmitted was invariably decreased by CETIEDIL, in the denervated or intact dog, indicating the direct myocardia impact of the substance. By comparison, quinidine is active only in the denervated animal, since as has been reported by DUCHENE-MARULLAZ, P., Therapie 1971, 26, 89–95 and 1193–1201, the vagolytic effects of the alkaloid enter into competition in the intact animal, resulting in a positive dromotropic tendency. During this study, the examination of other cardiac parameters shows the absence of any significant negative chronotropic effects with CETIEDIL, whilst quinidine has a positive or negative action according to whether the dog is intact or denervated, as also reported by DUCHENE-MARULLAZ. Finally, the effects on contractile force of the myocardia are slight with doses of 2.5 and 5 mg/kg, whilst with quinidine, as above, the effects are different according to whether the dog is denervated or intact.

Another important point must also be examined: the effects of CETIEDIL in calcium conductance. Previous studies had already shown the antagonism of the substance against the contraction inducing effects of calcium on vascular muscles. This was a competive antoganism which could be overcome by increasing the calcium concentration. This present study confirmed the remarkable action of CETIEDIL against ventricular fibrillation induced in the rat by calcium, a technique in which the substance proved to be the most active of all those used, capable of preventing rhythm abnormalities and death in all of the animals.

Finally, the use of Ouabain as an arrhythmogenic agent confirms previous studies. In the guinea pig and dog, CETIEDIL proves to be very active against ventricular tachycardia or the polymorphous extrasystoles induced by the cardiac glycoside in question. The latter is considered classically to act in three ways: cholinergic stimulation, central stimulation of adrenergic origin, direct action on the myocardia. There are a large number of arguments which tend to demonstrate (LUCCHESI, B. P., J. Pharmacol. Exp. Ther. 1965, 148, 94–99 and Benfey, A. M. et al, Brit, J. Pharmacol. 1966, 26, 3–8) that the antiarrhythmic action of a substance against Ouabain is not related to its tendency to produce adrenergic block. $\beta$-adrenergic inhibitors, in fact, oppose the arrhythmias induced by Ouabain but at doses which are significantly higher than those which produce adrenergic block (LUCCHESI et. al, B. P., Ann N.Y. Acad. Sci. 1967, 139, 940–951 and Raper, C. et al., European J. Pharmacol., 1968, 4, 1–12). The origin of the cardiotoxicity of the glycoside would appear to be essentially due to inhibition of ionic transport (APANTAKU et al., J. Pharmacol Exp. Ther. 1975, 193, 327, in which adrenergic mechanisms could nevertheless play a role (KAPLAN et al., J. Pharmacol, Exp. Ther. 1970, 175,168).

As with all membrane stabilizing agents, it may be understood that CETIEDIL is capable of overcoming arrhythmias due to Ouabain by prolonging the effective refractory period, the latter being abnormally decreased by cardiac glycosides which increase potassium conductance and the rate of repolarisation. It is possible that in the case of the CETIEDIL, the inhibitory effect on calcium conductance could be of importance since it has been shown (Borys Surawicz, M. B., Amer. Heart. J., 1973, 73, 814–834); that atrio-ventricular conduction disturbances, as well as ventricular facilitation, are caused by an increase in extra-cellular potassium. These effects are reversed or prevented by an increase in the extra-cellular calcium concentration. By inhibiting cellular calsium penetration, CETIEDIL increases extracellular calcium. On these bases CETIEDIL could be included in a second group of anti-drysrhthmic agents acting by inhibition of calcium penetration, a group in which the reference substance is Verapamil.

Possible inclusion in two anti-arrhythmic groups is known for other substances used therapeutically, which may have two different mechanisms of action.

CLINICAL SECTION

Figure 14:
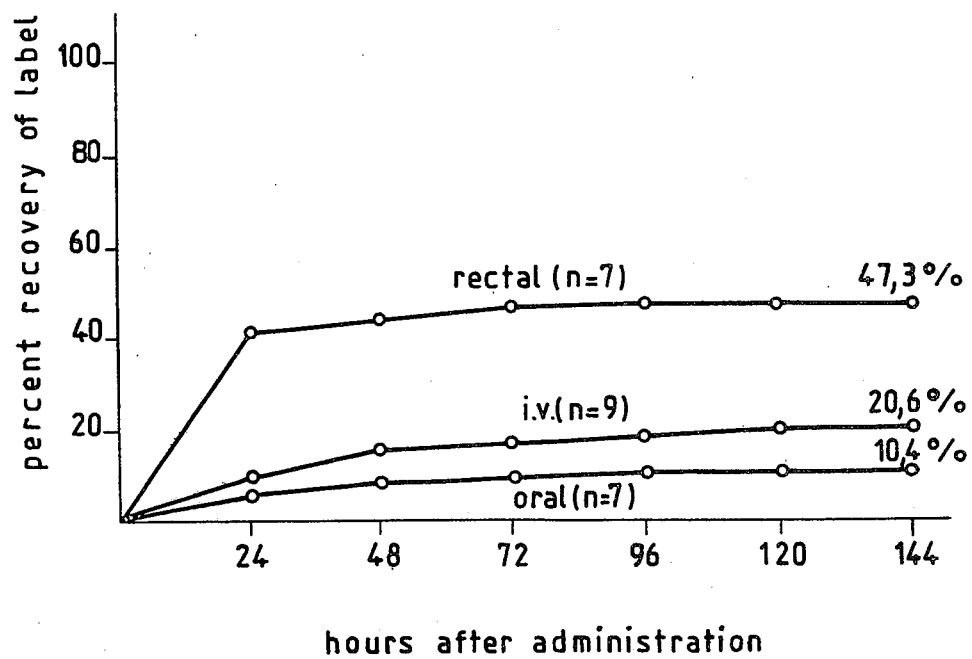

PHARMAKINETICS OF CETIEDIL (FIGS. 12, 13 and 14)

The pharmakinetics of CETIEDIL labelled with $C^{14}$, has been studied by J. R. BOISSIER et al., Wur. J. Med Chem., Chemical Therapeutica, 1974, 9, No. 5, 534–538 in the animal and by A. SOETERBOCK et al., European Journal of Clinical Pharmacology, Vol. 12, 205–208 (1977) in 9 healthy volunteers. Analysis of plasma radio-activity in man following the intravenous administration of 0.25 mg shows only two distinct exponential phases. The first is extremely short lived and the second is characterized by a terminal half-life of approximately five hours. However, urinary excretion is characterized by a much longer terminal half-life of the order of 26 hours. Thus in man, it is possible to accept the existence of a third deeper compartment. On the bases of experimental values, the distribution volume is 150 L (2.5 l/kg), but the true volume is certainly greater in view of the existence of a deeper compartment. In man, approximately 65% of the radio-activity is excreted in the urines. Biliary excretion, measured in an individual with a biliary drain is no more than 11%. However the existence of an entero-hepatic cycle cannot be excluded, by virtue of the fact that urinary excretion was lower in the patient who had undergone surgery (42%) than in those with an intact biliary circulation (65%).

METABOLISM

Metabolic studies show that by 5 minutes after the intravenous injection of 0.25 mg of CETIEDIL $C^{14}$, half of the circulating radio-activity is due to the presence of a metabolite. Urine passed 1 hour following the injection contains no CETIEDIL (100% radio-active transformation substance). On the bases of these data it may be concluded that CETIEDIL is rapidly transformed, both in the animal and in man.

BIOAVAILABILITY

The digestive absorbtion of CETIEDIL $C^{14}$ would appear to be excellent. It should nevertheless be mentioned that, following oral administration in man, plasma radioactivity is markedly higher than after intravenous injection. This phenomenon has been attributed to the "first pass effect". Following digestive absorption, a large fraction of the substance first passes into the liver where it is metabolized.

The radioactive metabolites thus formed diffuse in a volume which is smaller than the distribution volume of CETIEDIL. It follows that the plasma radioactivity does not represent CETIEDIL, but all of its metabolites together.

Rectal absorption of CETIEDIL would appear to be relatively low, and above all, very slow, as the plasma concentration fails to reach the threshold of detection.

THE TOLERANCE OF NORMAL HEALTHY ADULT MALE SUBJECTS TO CETIEDIL GIVEN BY INTRAVENOUS INFUSION (Lewis, G. P., Tufts University-Clinical Pharmacology Center Lemuel Stattuck Hospital.)(Tables 8 and 9)

SUMMARY

In 10 volunteers, cetiedil (average dose was 0.359 mg/kg) infused once a day for three consecutive days, and after four days of washout period, drug infused twice a day for three consecutive days, caused no significant abnormalities in electrocardiograms, in blood chemistry, in hematologic profiles, and in urine analyses. A doubtful elevation in SGOT value was obtained in 2 subjects after the completion of study-period, but other liver function tests were all normal.

In one subject, a minimal elevation of $Ca++$ was observed, while in another subject, a slight reduction in $K+$ level was observed after completing the study.

Dizziness, lightheadedness, blurred vision, dry mouth, numbness, heavy feeling on extremities and CNS effects (e.g., spacy feeling, feels as if 'walking on air' weird feeling, oozy feeling, feeling of drunkeness, and feels high) were complained of during the study. However, the duration of experiencing such side effects was only transitory: Side effects such as feels high, dry mouth, dizziness, lightheadedness, were complained of by 3 subjects for only 15 minutes in duration after the ninth infusion of cetiedil (0.359 mg/kg×9 infusions over a 10-day period). Contrarily, after the first infusion of cetiedil (0.359 mg/kg×1 on first day of the study), 7 subjects complained of side effects described as spacy feeling, high feeling, drunken feeling, weird feeling, blurred vision, lightheadedness, dizziness, floating feeling, double vision, numbness, and dry mouth for an average of 72.9 minutes after the completion of cetiedil infusion. It is apparent that a tolerance (or tachyphylaxis) was developing to the side effects.

Pulse rate was slightly reduced usually one hour after the infusion of cetiedil, and systemic blood pressure was also slightly decreased one to four hours after infusion of cetiedil. Such reductions cannot be called a clinical bradycardia or hypotension.

In conclusion, cetiedil, 0.359 mg/kg infused 9 times over a 10 day-period, was a safe drug. Atropine-like side effects, including, CNS effects, were transitory in nature and subjects tolerated the drug when given repeatedly. All these data should suggest the clinical use of Cetiedil, which is already in therapeutic use for peripheral diseases, in the treatment of some cardiac dysrythmias, particularly supraventricular arrythmias. The first clinical results are promissing. (example of E.K.G.): FIG. 15.

TABLE 1
POLYMORPHOUS ARRHYTHMIAS INDUCED IN THE ANAESTHETIZED GUINEA-PIG
(URETHANE 1.2 g/kg/IP)
BY THE COMBINATION OF
ADRENALINE PETROL-ETHER
COMPARISON OF ACTIVITY OF CETIEDIL
WITH REFERENCE SUBSTANCES

| SUB-STANCE*** | $ED_{50}$ mg/kg/IV* | $LD_{50}$ mg/kg/IV mouse | "I" $\frac{DL_{50}}{DE_{50}}$ | RELATIVE ACTIVITY** |
|---|---|---|---|---|
| CETIEDIL | 1.20 | 57 | 47.50 | 1 |
| Propranolol | 0.38 | 22 | 57.89 | 1.22 |
| Ajmaline | 0.60 | 26 | 43.33 | 0.91 |
| Quinidine | 4.20 | 67 | 15.95 | 0.34 |
| Procainamide | 1.40 | 105 | 75.00 | 1.58 |

$ED_{50}$ = theoretical dose capable of decreasing by half, in comparison with a control group, the duration of the disturbances induced

** = relative activity: $\frac{\text{"I" reference substance}}{\text{"I" Cetiedil}}$

*** = substance administered 5 minutes before intoxication
PROCAINAMIDE > PROPRANOLOL > CETIEDIL > AJMALINE > QUINIDINE TABLE 2
VENTRICULAR FIBRILLATION IN THE ANAESTHETIZED RAT INDUCED BY $CaCl_2$
MALINOW'S TECHNIQUE
PROTECTION AGAINST VENTRICULAR FIBRILLATION

| SUB-STANCE | AD 50* mg/kg/IV | LD 50 mg/kg/IV mouse | "I" $\frac{DL_{50}}{DA_{50}}$ | RELATIVE ACTIVITY** |
|---|---|---|---|---|
| CETIEDIL | 3,50 2,084–5,879 | 57 | 18,69 | 1 |
| Quinidine | 5,50 4,047–7,475 | 67 | 12,18 | 0,65 |
| Propranolol | 3,25 2,040–5,177 | 22 | 6,77 | 0,36 |
| Ajmaline | 2,25 1,562–3,241 | 26 | 11,56 | 0,62 |
| Procainamide | 14,50 8,368–26,177 | 105 | 7,24 | 0,39 |

*The AD 50 is the theoretical dose capable of preventing the development of ventricular fibrillation in 50% of the animals (calculated using the method of Litchfield and Wilcoxon) with intervals of confidence. (p = 0,05)

**Relative activity = $\frac{\text{"I" reference substance}}{\text{"I" Cetiedil}}$

CETIEDIL > QUINIDINE > AJMALINE > PROCAINAMIDE > PROPRANOLOL

TABLE 3
VENTRICULAR FIBRILLATION IN ANAESTHETIZED RAT INDUCED BY $CaCl_2$ (200 mg/kg I.V.)
MALINOW'S TECHNIQUE
PROTECTION AGAINST DEATH

| SUB-STANCE | $AD_{50}$* mg/kg/IV | LD 50 mg/kg/IV mouse | "I" $\frac{DL_{50}}{DA_{50}}$ | RELATIVE ACTIVITY** |
|---|---|---|---|---|
| CETIEDIL | 3.5 (2,084–5,879) | 57 | 16.29 | 1.00 |
| Quinidine | 8.0 (4,958–12,909) | 67 | 8.38 | 0.51 |
| Propranolol | 3.9 (3,044–4,997) | 22 | 5.64 | 0.35 |
| Ajmaline | $DA_0 > 5$ | 26 | — | — |
| Procainamide | 17,0 (12,878–22,441) | 105 | 6.18 | 0.38 |

*The $AD_{50}$ is the theoretical dose capable of preventing the development of death in 50% of the animals (calculated using the method of Litchfield and Wilcoxon) with intervals of confidence

**Relative activity = $\frac{\text{"I" reference substance}}{\text{"I" Cetiedil}}$

CETIEDIL > QUINIDINE > PROCAINAMIDE > PROPRANOLOL > AJMALINE

TABLE 4
VENTRICULAR TACHYCARDIA INDUCED BY OUABAINE IN THE ANESTHETIZED GUINEA-PIG
(URETHANE 1.2 g/kg/IP)

| SUBSTANCE | DOSE mg/kg -IV- 2 minutes before slow infusion+ | Ventricular tachycardia of μg of ouabaine/kg++ |
|---|---|---|
| CONTROL | | 193.30 ± 11,16 |
| CETIEDIL | 5.0 | 263.80 ± 25,15* |
| " | 10.0 | 281.80 ± 19,13* |
| AJMALINE | 2.5 | 310.67 ± 18,73** |
| " | 5.0 | 329.00 ± 6,66** |
| QUINIDINE | 3.0 | 222.00 ± 6,00 |
| " | 5.0 | 229.00 ± 18,33 |
| PROCAINAMIDE | 5.0 | 273.67 ± 18,27* |

*p < 0,01
**p < 0,001
+Slow infusion of a 40 μg/ml solution of ouabain at a rate of 0.5 ml/min
++Dose of ouabain required to produce ventricular tachycardia in the anesthetize guinea-pig.

TABLE 5
COMPARISON OF THE EFFECTS OF CETIEDIL WITH THOSE OF REFERENCE SUBSTANCES ON THE STIMULATED ISOLATED GUINEA PIG ATRIAL

| SUBSTANCE | % DECREASE SPONTANEOUS RATE | | | % DECREASE m.f.s | | |
|---|---|---|---|---|---|---|
| | $10^{-7}$ | $10^{-6}$ | $10^{-5}$ | $10^{-7}$ | $10^{-6}$ | $10^{-5}$ |
| CETIEDIL | 9 | 6 | 26 | 6 | 14 | 27 |
| QUINIDINE | 0 | 3 | 15 | — | 10 | 25 |
| DISOPYRAMIDE | — | 6 | 8 | — | 6 | 18 |
| PROPANOLOL | not measured | | | 7 | 34 | — | m.f.s = maximum frequency followed by the atrial with a rhythm 1/1 - (stimulation/contraction)

TABLE 6
TABLE SUMMARISING ANAESTHESIC ACTIVITY

| SUBSTANCE | CONCENTRATIONS g./100 | pH | TOTAL DEGREE OF ANAESTHESIA FOR 60 minutes** |
|---|---|---|---|
| CETIEDIL | 0.25 | 4.5 | 393.2 |
| CETIEDIL | 0.50 | 4.0 | 798.8 |
| COCAINE | 1.00 | 5.5 | 706.4 |
| PROCAINE | 1.00 | 5.5 | 61.5 |
| PROPRANOLOL | 1.00 | 5.0 | 876.5 |

**total 13: no anaesthesia
total 1300: complete anaesthesia for 60 minutes.

TABLE 7
INHIBITION BY CETIEDIL OF CONTRACTION OF RAT AORTA FRAGMENT INDUCED BY POTASSIUM DEPOLARISATION

| EXPERIMENT N° | CETIEDIL CONCENTRATION | $pD_x$ | x | $pD'_2$ |
|---|---|---|---|---|
| 1 | 10 | 5.00 | 2.78 | 5.25 |
| 2 | 5 | 5.30 | 1.50 | 5.00 |
| 2 | 10 | 5.00 | 3.24 | 5.35 |
| 3 | 1 | 6.00 | 1.16 | 5.20 |
| 3 | 5 | 5.30 | 2.17 | 5.37 |
| 3 | 10 | 5.00 | 2.70 | 5.23 |
| MEAN ± SD ± D.S. | | | | 5.23 ± 0,05 |

CETIEDIL $pD'_2 = 5.23 \pm 0.05$
PROCAINE $pD'_2 = 2.55 \pm 0.06$
*$pD'_2 = pD_x + \log(x - 1)$
$pD_x = -\log$ of Cetiedil concentration
$x = $ ratio $\frac{\text{maximum effect without inhibitor}}{\text{maximum effect with inhibitor}}$

TABLE 8
DEMOGRAPHY OF TEN VOLUNTEERING SUBJECTS (MALES)

| Subject No. | Age | Weight (kg) | Height (cm) | Race | Cetiedil Received (mg/kg per infusion) |
|---|---|---|---|---|---|
| 1 | 20 | 74.2 | 171.5 | Black | 0.337 |
| 2 | 26 | 71.1 | 168.9 | White | 0.352 |
| 3 | 30 | 72.9 | 174.0 | Puerto Rican | 0.343 |
| 4 | 21 | 65.8 | 176.5 | Black | 0.380 |
| 5 | 24 | 67.8 | 182.9 | Black | 0.369 |
| 6 | 29 | 74.2 | 181.0 | White | 0.337 |
| 7 | 19 | 64.7 | 174.6 | White | 0.386 |
| 8 | 32 | 68.0 | 186.1 | White | 0.368 |
| 9 | 21 | 64.0 | 180.3 | White | 0.391 |
| 10 | 24 | 76.9 | 178.4 | Amer. Indian | 0.325 |
| Mean ± S. E. M. | 24.6 ±1.43 | 69.96 ±1.429 | 177.42 ±1.683 | — | 0.359 ±0.0073 |

(All Male Subjects; 5 Whites; 3 Blacks; 1 Puerto Rican 1 American Indian).
In 10 volunteers, CETIEDIL (average dose was 0.359 mg/kg) infused once a day for three consecutive days, and after four days of washout period, drug infused twice a day for three consecutive days.

TABLE 9
THE TOLERANCE OF NORMAL HEALTHY ADULT MALE SUBJECTS TO CETIEDIL GIVEN BY INTRAVENOUS INFUSION STUDY PROTOCOL

| HEMODYNAMICS* | BLOOD CHEMISTRY** | HEMATOLOGY** | URINALYSIS** |
|---|---|---|---|
| | Ca ++ mg % | | |
| | PHOS mg % | WBC × $10^3$ | |
| | GLUCOSE mg % | | |
| - SYSTOLIC | BUN mg % | | |
| DIASTOLIC | URIC ACID mg % | RBC × $10^6$ | |
| BLOOD | CHOLESTEROL mg % | | |
| PRESSURES | TOT BILIRUBIN mg % | Hgb gm % | |
| (Standing | ALK. PHOS. mU/ml | | |
| Position) | LDH mU/ml | Hct % | |
| - PULSE RATE | | MCV $\mu^3$ | |
| (Standing | SGOT mU/ml | | |
| Position) | CPK mU/ml | | WBC/HPF |
| | SGPT mU/ml | MCH$\mu$ $\mu$g | RBC/HPF |
| - RESPIRATORY | | | |
| RATE | CREATININE mg % | MCHC % | |
| | SODIUM meq/L | | EPITH CELLS |
| | POTASSIUM meq/L | NEUTROPHILES % | |
| - E C G | | | CRYSTALS |
| | CHLORIDE meq/L | BANDS % | |
| | $CO_2$ meq/L | | |
| | TRIGLYCERIDES mg % | LYMPHS % | BACTERIA |
| | PBI SERUM $\mu$g % | | |
| | $T_3$ SERUM % | MONOS % | MUCUS |
| | $T_4$ SERUM $\mu$g % | | |
| | SEROLOGY (RPR) | EOS % | |
| | TOT PROTEIN gm % | BASOS % | |
| | ALBUMIN gm % | RBC MORPHOLOGY | |

*Before and 1, 2, 4, 6 and 12 hours after the CETIEDIL infusion intravenously.
**Before and at the end of the study period.

According to the present invention, CETIEDIL can be used for the treatment of troubles of cardiac rhythm, i.e. cardiac arrhythmia, particularly sinusal, atrial or supraventicular dyrhythmias, and ventricular tachyarrhythmias. Moreover cetiedil can be used in disturbances observed during treatment by cardiotonics.

It can be administered in the form of tablets, capsules, gelatin-coated pills for the purpose of oral administration or in the form of injectable solutions for intramuscular or intravenous route with appropriate excipients. The unit dose can be 5 to 50 mg for injections and approximately 50 to 150 mg for oral administration.

The following are Examples of pharmaceutical compositions:

EXAMPLE 1

| Injectable solution | |
|---|---|
| Cetiedil | 25 mg |
| Isotonic NaCl solution to | 5 ml. |

EXAMPLE 2

| Gelatin-coated pill | |
|---|---|
| Cetiedil | 100 mg |
| "Aerosil" (Registered Trade Mark) | 3 mg. |
| Lactose | 21 mg. |
| Magnesium stereate for 1 gelatin-coated pill N°. 2 (i.e. 0.37 ml) | 6 mg. |

The daily posology can range from 5 to 100 mg, especially 25 to 100 mg for injections and 50 to 600 mg for oral administration.

What I claim:

1. A method for treating a patient for cardiac arrhythmia which comprises administering to the said patient a therapeutically effective dose of cetiedil, the mode of administration being oral or injection.

2. A method of claim 1 in which the oral dosage unit is 50 to 150 mg.

3. A method of claim 1 in which the injected dosage unit is from 5 to 50 mg.

* * * * *